United States Patent
Iwaya et al.

(10) Patent No.: US 12,064,084 B2
(45) Date of Patent: Aug. 20, 2024

(54) ULTRASOUND ENDOSCOPE

(71) Applicant: FUJIFILM Corporation, Tokyo (JP)

(72) Inventors: Tatsuhiro Iwaya, Ashigarakami-gun (JP); Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 596 days.

(21) Appl. No.: 17/381,328

(22) Filed: Jul. 21, 2021

(65) Prior Publication Data
US 2022/0071472 A1    Mar. 10, 2022

(30) Foreign Application Priority Data

Sep. 8, 2020  (JP) ................................. 2020-150292

(51) Int. Cl.
*A61B 1/00*   (2006.01)
*A61B 8/00*   (2006.01)

(52) U.S. Cl.
CPC ........ *A61B 1/0008* (2013.01); *A61B 1/00114* (2013.01); *A61B 8/4483* (2013.01); *A61B 2562/164* (2013.01); *A61B 2562/182* (2013.01)

(58) Field of Classification Search
CPC . A61B 1/0008; A61B 1/00114; A61B 8/4483; A61B 2562/164; A61B 2562/182;
(Continued)

(56) References Cited

U.S. PATENT DOCUMENTS 5,614,660 A * 3/1997 Tanaka ............... A61B 8/4281
                                                    604/165.01
5,766,151 A * 6/1998 Valley ............... A61M 39/0247
                                                    604/103.07
(Continued)

FOREIGN PATENT DOCUMENTS

JP      62-78909 U      5/1987
JP      2012-146591 A   8/2012
(Continued)

OTHER PUBLICATIONS

Japanese Office Action for corresponding Japanese Application No. 2020-150292, dated Mar. 20, 2023, with English translation.
(Continued)

*Primary Examiner* — Sanjay Cattungal
(74) *Attorney, Agent, or Firm* — Birch, Stewart, Kolasch & Birch, LLP

(57) ABSTRACT

An ultrasound endoscope includes an insertion part including a distal end part having an ultrasound transducer array of ultrasound transducers, a cable inserted into the insertion part, and a substrate, including electrode pads, that electrically connects the ultrasound transducers and the cable, and is disposed in the distal end part. The cable has a non-coaxial cable including a first cable bundle consisting of signal wires and ground wires, and a first shield layer with which the first cable bundle is coated, and an outer coat with which a second cable bundle consisting of the non-coaxial cables is coated. Each first cable bundle is individually led out from the cable, and each signal wire of the first cable bundle is led out and electrically bonded to the corresponding electrode pad. The ultrasound endoscope further includes a fixing part that fixes relative positions of the substrate and each first cable bundle.

16 Claims, 12 Drawing Sheets

(58) Field of Classification Search
CPC ......... A61B 8/12; A61B 8/445; A61B 8/4494; A61B 8/44; A61B 8/56; B06B 1/0622; B06B 1/0207
See application file for complete search history.

(56) References Cited

U.S. PATENT DOCUMENTS

| | | | | |
|---|---|---|---|---|
| 5,879,499 | A * | 3/1999 | Corvi | A61M 25/0012 604/524 |
| 6,142,945 | A * | 11/2000 | Sakamoto | A61B 8/445 600/459 |
| 11,583,245 | B2 * | 2/2023 | Hadani | A61B 8/445 |
| 2003/0045768 | A1 * | 3/2003 | Hirooka | A61B 8/4245 600/2 |
| 2006/0195016 | A1 * | 8/2006 | Fujikura | A61B 1/00082 600/116 |
| 2007/0249940 | A1 * | 10/2007 | Kohno | A61B 1/00098 600/463 |
| 2008/0058591 | A1 * | 3/2008 | Saadat | A61B 17/0057 600/109 |
| 2009/0099414 | A1 * | 4/2009 | Goto | A61B 10/06 600/114 |
| 2010/0331883 | A1 * | 12/2010 | Schmitz | A61B 17/320758 606/279 |
| 2012/0292104 | A1 | 11/2012 | Yamada | |
| 2013/0244456 | A1 | 9/2013 | Sakamoto | |
| 2013/0333917 | A1 | 12/2013 | Tanabe | |
| 2014/0018788 | A1 * | 1/2014 | Engelman | A61B 18/1492 606/33 |
| 2016/0016016 | A1 * | 1/2016 | Taylor | A61B 17/320068 606/169 |
| 2019/0038257 | A1 | 2/2019 | Yamamoto et al. | |
| 2019/0047021 | A1 | 2/2019 | Yamamoto et al. | |
| 2019/0133558 | A1 * | 5/2019 | Morimoto | A61B 8/12 |
| 2019/0133559 | A1 * | 5/2019 | Okada | H10N 30/06 |
| 2020/0205777 | A1 | 7/2020 | Kumata | |
| 2020/0405136 | A1 | 12/2020 | Sakamoto | |

FOREIGN PATENT DOCUMENTS

| | | |
|---|---|---|
| JP | 2012-243465 A | 12/2012 |
| JP | 2013-215555 A | 10/2013 |
| JP | 2019-54962 A | 4/2019 |
| WO | WO 2012/120993 A1 | 9/2012 |
| WO | WO 2016/143133 A1 | 9/2016 |
| WO | WO 2017/187755 A1 | 11/2017 |
| WO | WO 2017/187756 A1 | 11/2017 |
| WO | WO 2018/003232 A1 | 1/2018 |
| WO | WO 2019/187629 A1 | 10/2019 |

OTHER PUBLICATIONS

Japanese Office Action for corresponding Japanese Application No. 2023-122517, dated Mar. 26, 2024, with English translation.

* cited by examiner

ULTRASOUND ENDOSCOPE

CROSS-REFERENCE TO RELATED APPLICATIONS

The present application claims priority under 35 U.S.C § 119 to Japanese Patent Application No. 2020-150292 filed on Sep. 8, 2020. The above application is hereby expressly incorporated by reference, in its entirety, into the present application.

BACKGROUND OF THE INVENTION

1. Field of the Invention

The present invention relates to an ultrasound endoscope.

2. Description of the Related Art

In recent years, an ultrasound endoscope that observes a state inside a body of a subject by irradiating the inside of the body with ultrasonic waves and receives reflected waves to capture video has been used in medical practice.

For example, as disclosed in JP2019-054962A, such an ultrasound endoscope comprises a distal end part that comprises piezoelectric elements configuring ultrasound transducers, a bending part and a flexible part connected to a proximal end of the distal end part, a plurality of coaxial cables that are inserted into the bending part and the flexible part, and a wiring substrate that electrically connects the piezoelectric elements and the coaxial cables.

SUMMARY OF THE INVENTION

Incidentally, a coaxial cable is formed by covering a shield layer and an outer coat the periphery of one signal wire coated for insulation. For this reason, the outside diameter of the coaxial cable increases, and the ultrasound endoscope is hardly reduced in diameter.

Accordingly, a case where an ultrasound endoscope is reduced in diameter by applying a non-coaxial cable instead of the coaxial cable is considered. However, the non-coaxial cable does not comprise the shield layer and the outer coat for each one signal wire. For this reason, there is a problem in that the non-coaxial cable is likely to be disconnected at the time of connection to a wiring substrate.

The invention has been accomplished in view of such a situation, and an object of the invention is to provide an ultrasound endoscope capable of preventing a non-coaxial cable from being disconnected and achieving reduction in diameter.

An ultrasound endoscope of a first aspect comprises an insertion part that includes a distal end part having an ultrasound transducer array in which a plurality of ultrasound transducers are arranged, a cable that is inserted into the insertion part, and a substrate that electrically connects the plurality of ultrasound transducers and the cable, and is disposed in the distal end part. The cable has a non-coaxial cable that includes a first cable bundle consisting of a plurality of signal wires and a plurality of ground wires, and a first shield layer with which the first cable bundle is coated, and an outer coat with which a second cable bundle consisting of a plurality of the non-coaxial cables is coated. The substrate includes a plurality of electrode pads connected to the plurality of ultrasound transducers, respectively. Each first cable bundle is individually led out from the cable, and each signal wire of the first cable bundle is led out and electrically bonded to the corresponding electrode pad of the substrate. A fixing part that fixes relative positions of the substrate and each first cable bundle is provided.

In an ultrasound endoscope of a second aspect, the cable includes a second shield layer with which the second cable bundle is coated, between the outer coat and the second cable bundle.

In an ultrasound endoscope of a third aspect, the cable includes a resin layer with which the second cable bundle is coated, between the second cable bundle and the second shield layer.

In an ultrasound endoscope of a fourth aspect, the cable includes a resin layer with which the second cable bundle is coated, between the outer coat and the second cable bundle.

In an ultrasound endoscope of a fifth aspect, the resin layer is made of a fluorine-based resin material.

In an ultrasound endoscope of a sixth aspect, the fixing part is any one of an adhesive, solder, or a clamp member, or a combination thereof.

In an ultrasound endoscope of a seventh aspect, the fixing part fixes the substrate and each first cable bundle in a state in which a part of the first cable bundle is superimposed on the substrate.

In an ultrasound endoscope of an eighth aspect, the fixing part fixes the substrate and each first cable bundle in a state in which a part of the first cable bundle is not superimposed on the substrate.

In an ultrasound endoscope of a ninth aspect, the substrate is any one of a rigid substrate or a flexible substrate.

In an ultrasound endoscope of a tenth aspect, distances between the electrode pads of the substrate corresponding to the plurality of signal wires included in each first cable bundle and a distal end of the first cable bundle fixed by the fixing part are equal for each first cable bundle.

In an ultrasound endoscope of an eleventh aspect, there are two kinds or more of distances between the electrode pads of the substrate corresponding to the plurality of signal wires included in each first cable bundle and a distal end of the first cable bundle fixed by the fixing part, for each first cable bundle.

In an ultrasound endoscope of a twelfth aspect, the substrate has a ground electrode pad, and at least one ground wire included in each first cable bundle is electrically bonded to the ground electrode pad.

In an ultrasound endoscope of a thirteenth aspect, the ground wires that are included in each first cable bundle and are not bonded to the ground electrode pad are connected between the ground electrode pad and the distal end of the first cable bundle fixed by the fixing part.

In an ultrasound endoscope of a fourteenth aspect, there are two kinds or more of the distances different between the first cable bundles.

In an ultrasound endoscope of a fifteenth aspect, the signal wires included in the first cable bundle are at least unequal in electric capacity per unit length, and for the signal wire smaller in the electric capacity per unit length among the signal wires of the first cable bundle, the distance between the electrode pad and the distal end of the first cable bundle fixed by the fixing part is longer.

In an ultrasound endoscope of a sixteenth aspect, the substrate has grooves that hold the first cable bundles.

With the ultrasound endoscope according to the aspects of the invention, it is possible to prevent a non-coaxial cable from being disconnected and to achieve reduction in diameter.

DESCRIPTION OF THE PREFERRED EMBODIMENTS

Hereinafter, a preferred embodiment of an ultrasound endoscope according to the invention will be described referring to the accompanying drawings.

Figure 1:
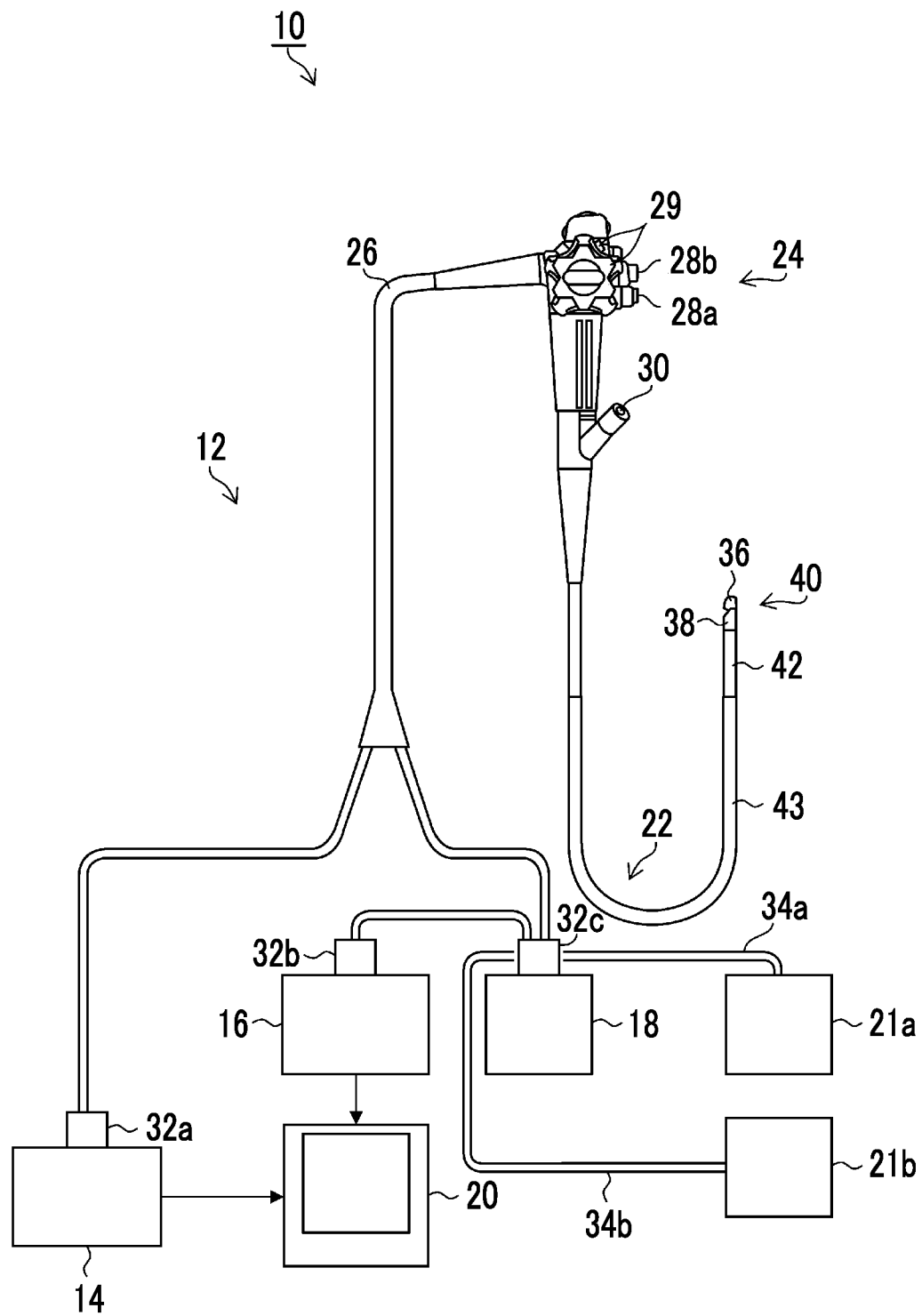
FIG. 1 is a schematic configuration diagram showing an example of the configuration of an ultrasonography system.

FIG. 1 is a schematic configuration diagram showing an example of an ultrasonography system 10 that uses an ultrasound endoscope 12 of an embodiment.

As shown in FIG. 1, the ultrasonography system 10 comprises an ultrasound endoscope 12, an ultrasound processor device 14 that generates an ultrasound image, an endoscope processor device 16 that generates an endoscope image, a light source device 18 that supplies illumination light, with which the inside of a body cavity is illuminated, to the ultrasound endoscope 12, and a monitor 20 that displays the ultrasound image and the endoscope image. The ultrasonography system 10 comprises a water supply tank 21a that stores cleaning water or the like, and a suction pump 21b that sucks aspirates inside the body cavity.

The ultrasound endoscope 12 has an insertion part 22 that is inserted into the body cavity of the subject, an operating part 24 that is consecutively provided in a proximal end portion of the insertion part 22 and is used by an operator to perform an operation, and a universal cord 26 that has one end connected to the operating part 24.

In the operating part 24, an air and water supply button 28a that opens and closes an air and water supply pipe line (not shown) from the water supply tank 21a, and a suction button 28b that opens and closes a suction pipe line (not shown) from the suction pump 21b are provided side by side. In the operating part 24, a pair of angle knobs 29 and 29 and a treatment tool insertion port 30 are provided.

In the other end portion of the universal cord 26, an ultrasound connector 32a that is connected to the ultrasound processor device 14, an endoscope connector 32b that is connected to the endoscope processor device 16, and a light source connector 32c that is connected to the light source device 18 are provided. The ultrasound endoscope 12 are attachably and detachably connected to the ultrasound processor device 14, the endoscope processor device 16, and the light source device 18 respectively through the connectors 32a, 32b, and 32c. The connector 32c comprises an air and water supply tube 34a that is connected to the water supply tank 21a, and a suction tube 34b that is connected to the suction pump 21b.

The insertion part 22 has, in order from a distal end side, a distal end part 40 having an ultrasound observation part 36 and an endoscope observation part 38, a bending part 42 that is consecutively provided on a proximal end side of the distal end part 40, and a flexible part 43 that couples a proximal end side of the bending part 42 and the distal end side of the operating part 24.

The bending part 42 is remotely bent and operated by rotationally moving and operating a pair of angle knobs 29 and 29 provided in the operating part 24. With this, the distal end part 40 can be directed in a desired direction.

The ultrasound processor device 14 generates and supplies an ultrasound signal for making an ultrasound transducer array 50 of an ultrasound transducer unit 46 (see FIG. 2) of the ultrasound observation part 36 described below generate an ultrasonic wave. The ultrasound processor device 14 receives and acquires an echo signal reflected from an observation target part irradiated with the ultrasonic wave, by the ultrasound transducer array 50 and executes various kinds of signal processing on the acquired echo signal to generate an ultrasound image that is displayed on the monitor 20.

The endoscope processor device 16 receives and acquires a captured image signal acquired from the observation target part illuminated with illumination light from the light source device 18 in the endoscope observation part 38 and execute various kinds of signal processing and image processing on the acquired image signal to generate an endoscope image that is displayed on the monitor 20.

The ultrasound processor device 14 and the endoscope processor device 16 are configured with two devices (computers) provided separately. Note that the invention is not limited thereto, and both the ultrasound processor device 14 and the endoscope processor device 16 may be configured with one device.

To image an observation target part inside a body cavity using the endoscope observation part 38 to acquire an image signal, the light source device 18 generates illumination light, such as white light including light of three primary colors of red light, green light, and blue light or light of a specific wavelength. Light propagates through a light guide (not shown) and the like in the ultrasound endoscope 12, and is emitted from the endoscope observation part 38, and the observation target part inside the body cavity is illuminated with light.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

Next, the configuration of the distal end part 40 will be described referring to FIGS. 2 to 4.

Figure 2:
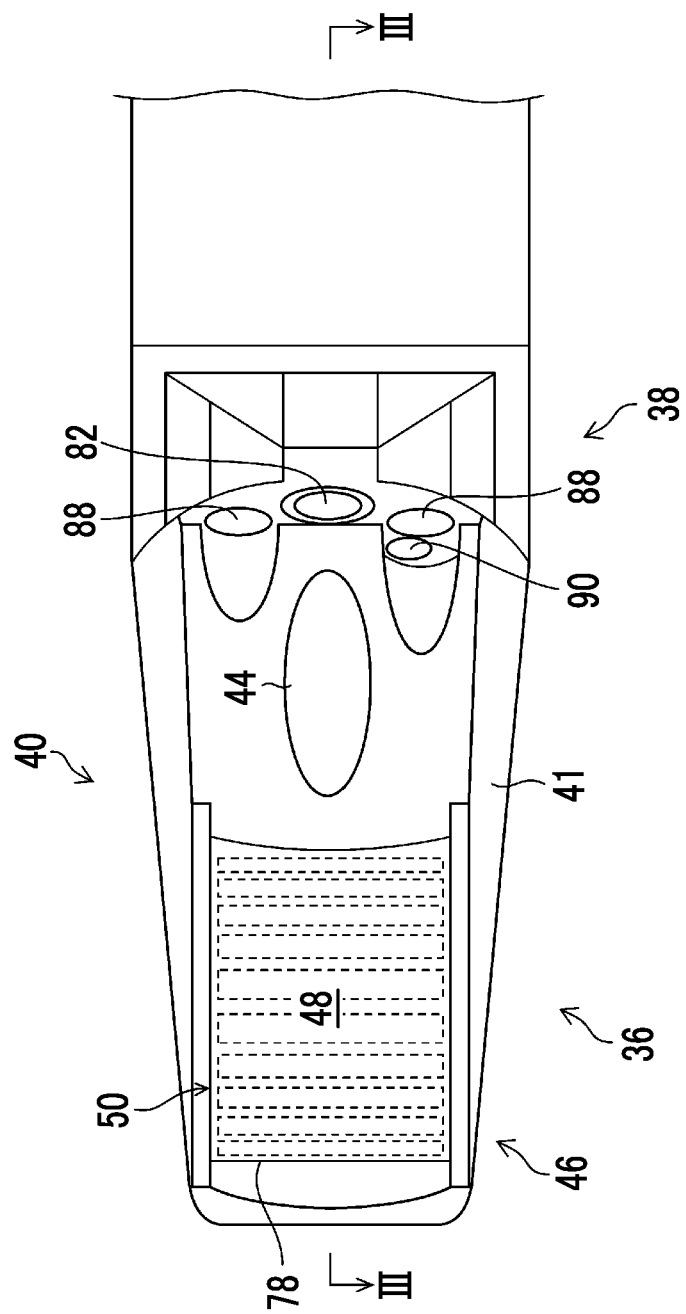
FIG. 2 is a partial enlarged plan view showing a distal end part of an ultrasound endoscope of FIG. 1 and the vicinity of the distal end part.

FIG. 2 is a partial enlarged plan view showing the distal end part 40 shown in FIG. 1 and the vicinity thereof the distal end part 40. FIG. 3 is a cross-sectional view taken along the line III-III shown in FIG. 2, and is a longitudinal sectional view of the distal end part 40 taken along a center line thereof in a longitudinal axis direction. FIG. 4 is a cross-sectional view taken along the line IV-IV shown in FIG. 3, and is a cross-sectional view of the ultrasound transducer array 50 of the ultrasound observation part 36 of the distal end part 40 taken along a center line of an arc structure.

Figure 3:
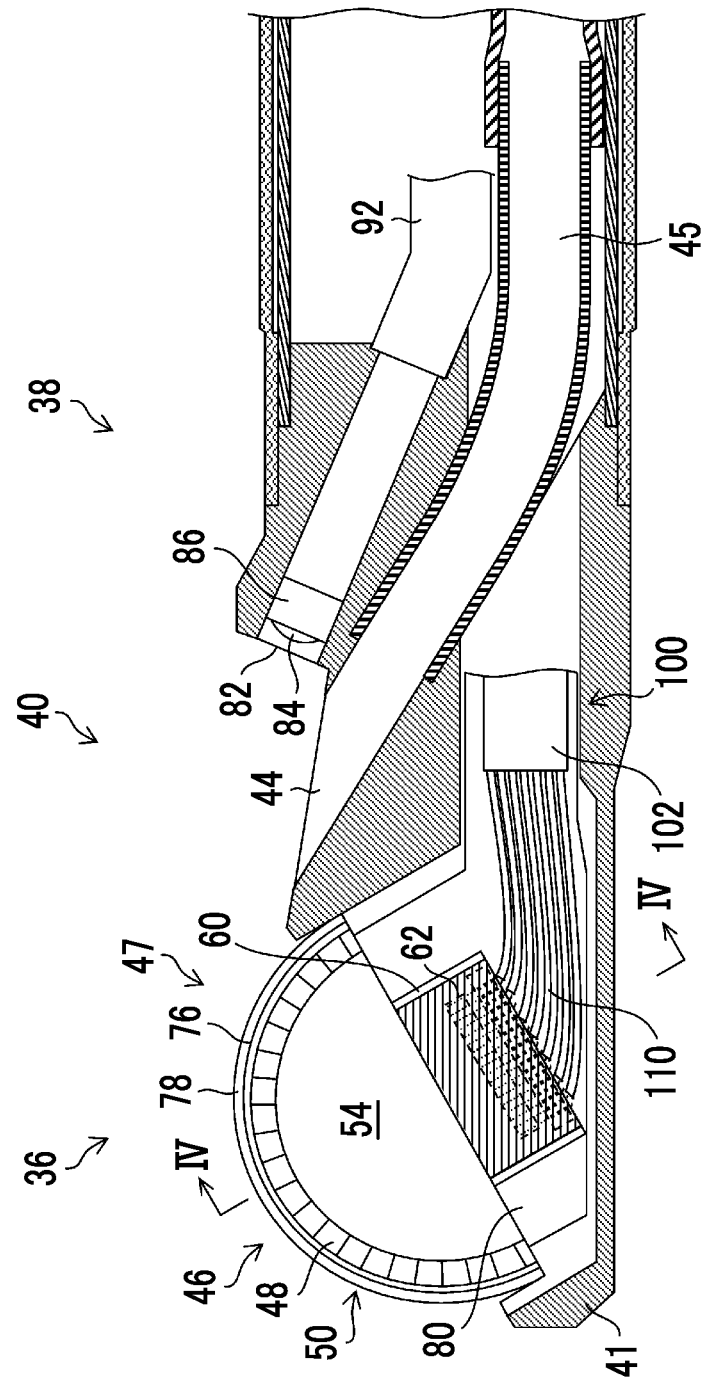
FIG. 3 is a cross-sectional view taken along the line III-III of FIG. 2.

As shown in FIGS. 2 and 3, in the distal end part 40, the ultrasound observation part 36 that acquires an ultrasound image is mounted on the distal end side, and the endoscope observation part 38 that acquires an endoscope image is mounted on the proximal end side. In the distal end part 40, a treatment tool lead-out port 44 is provided between the ultrasound observation part 36 and the endoscope observation part 38.

The endoscope observation part 38 is configured with an observation window 82, an objective lens 84, a solid-state imaging element 86, illumination windows 88, a cleaning nozzle 90, a wiring cable 92, and the like.

The treatment tool lead-out port 44 is connected to a treatment tool channel 45 that is inserted into the insertion part 22. A treatment tool (not shown) inserted from the treatment tool insertion port 30 of FIG. 1 is let out from the treatment tool lead-out port 44 into the body cavity through the treatment tool channel 45.

Figure 4:
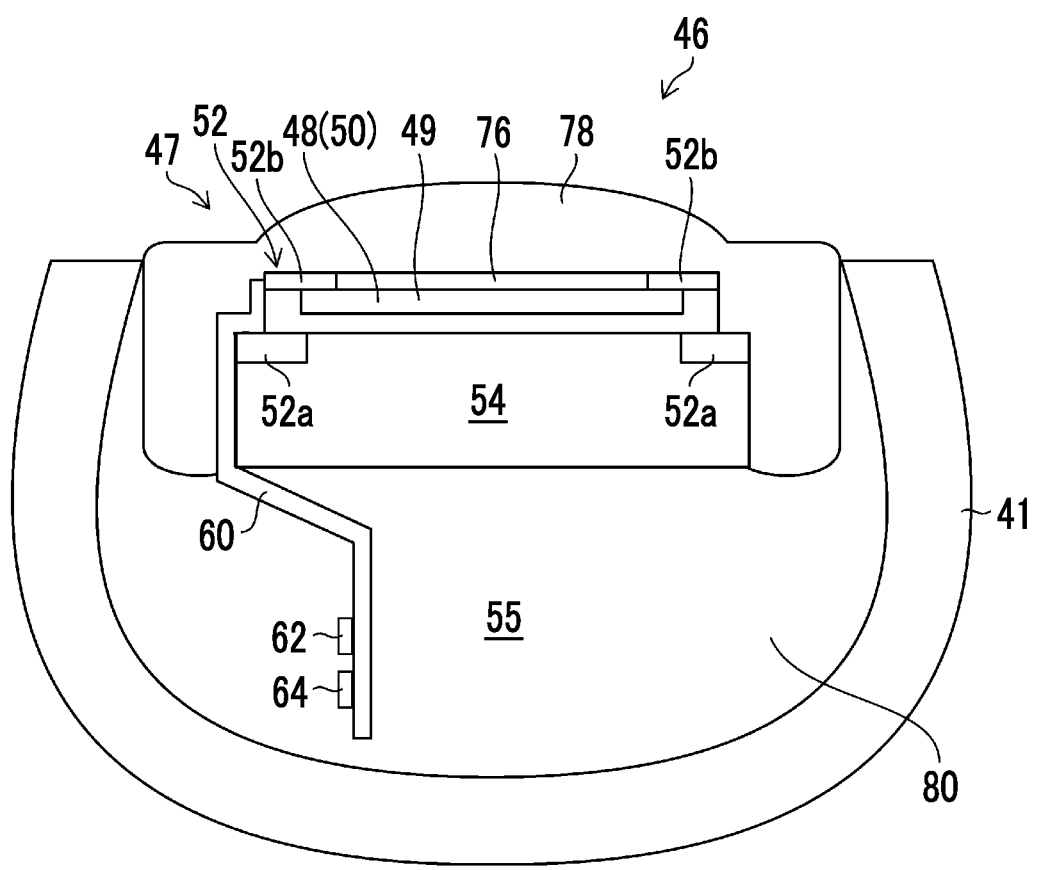
FIG. 4 is a cross-sectional view taken along the line IV-IV shown in FIG. 3.

As shown in FIGS. 2 to 4, the ultrasound observation part 36 comprises the ultrasound transducer unit 46, an exterior member 41 that holds the ultrasound transducer unit 46, and a cable 100 that is electrically connected to the ultrasound transducer unit 46 through a substrate 60. The exterior member 41 is made of a rigid member, such as rigid resin, and configures a part of the distal end part 40.

The ultrasound transducer unit 46 has the ultrasound transducer array 50 that consists of a plurality of ultrasound transducers 48, an electrode 52 that is provided on an end side of the ultrasound transducer array 50 in a width direction (a direction perpendicular to the longitudinal axis direction of the insertion part 22), a backing material layer 54 that supports each ultrasound transducer 48 from a lower surface side, the substrate 60 that is disposed along a side surface of the backing material layer 54 in the width direction and is connected to the electrode 52, and a filler layer 80 with which an internal space 55 between the exterior member 41 and the backing material layer 54 is filled.

As long as the substrate 60 can electrically connect a plurality of ultrasound transducers 48 and the cable 100, in particular, the structure thereof is not limited.

It is preferable that the substrate 60 is configured with, for example, a wiring substrate, such as a flexible substrate (flexible print substrate (also referred to as a flexible printed circuit (FPC)) having flexibility, a printed wiring circuit substrate (also referred to as a printed circuit board (PCB)) made of a rigid substrate having high rigidity with no flexibility, or a printed wiring substrate (also referred to as a printed wired board (PWB)).

The ultrasound transducer unit 46 has an acoustic matching layer 76 laminated on the ultrasound transducer array 50, and an acoustic lens 78 laminated on the acoustic matching layer 76. That is, the ultrasound transducer unit 46 is configured as a laminate 47 having the acoustic lens 78, the acoustic matching layer 76, the ultrasound transducer array 50, and the backing material layer 54.

The ultrasound transducer array 50 is configured with a plurality of rectangular parallelepiped ultrasound transducers 48 arranged in a convex arc shape outward. The ultrasound transducer array 50 is an array of 48 to 192 channels consisting of 48 to 192 ultrasound transducers 48, for example. Each of the ultrasound transducer 48 has a piezoelectric body 49.

The ultrasound transducer array 50 has the electrode 52. The electrode 52 has an individual electrode 52*a* individually and independently provided for each ultrasound transducer 48, and a transducer ground 52*b* that is a common electrode common to all the ultrasound transducers 48. In FIG. 4, a plurality of individual electrodes 52*a* are disposed on lower surfaces of end portions of a plurality of ultrasound transducers 48, and the transducer ground 52*b* is disposed on upper surfaces of the end portions of the ultrasound transducers 48.

The substrate 60 has 48 to 192 wirings (not shown) that are electrically connected to the individual electrodes 52*a* of the 48 to 192 ultrasound transducers 48, respectively, and a plurality of electrode pads 62 that are connected to the ultrasound transducers 48 through the wirings, respectively.

The ultrasound transducer array 50 has a configuration in which a plurality of ultrasound transducers 48 are arranged at a predetermined pitch in a one-dimensional array as an example. The ultrasound transducers 48 configuring the ultrasound transducer array 50 are arranged at regular intervals in a convex bent shape along an axial direction of the distal end part 40 (the longitudinal axis direction of the insertion part 22) and are sequentially driven based on drive signals input from the ultrasound processor device 14 (see FIG. 1). With this, convex electronic scanning is performed with a range where the ultrasound transducers 48 shown in FIG. 2 are arranged, as a scanning range.

The acoustic matching layer 76 is a layer that is provided for taking acoustic impedance matching between the subject and the ultrasound transducers 48.

The acoustic lens 78 is a lens that is provided for converging the ultrasonic waves emitted from the ultrasound transducer array 50 toward the observation target part. The acoustic lens 78 is formed of, for example, silicon-based resin (millable type silicon rubber, liquid silicon rubber, or the lie), butadiene-based resin, or polyurethane-based resin. In the acoustic lens 78, powder, such as titanium oxide, alumina, or silica, is mixed as necessary. With this, the acoustic lens 78 can take acoustic impedance matching between the subject and the ultrasound transducers 48 in the acoustic matching layer 76, and can increase the transmittance of the ultrasonic waves.

As shown in FIGS. 3 and 4, the backing material layer 54 is disposed on an inside with respect to the arrangement surface of a plurality of ultrasound transducers 48, that is, a rear surface (lower surface) of the ultrasound transducer array 50. The backing material layer 54 is made of a layer of a member made of a backing material. The backing material layer 54 has a role of mechanically and flexibly supporting the ultrasound transducer array 50 and attenuating ultrasonic waves propagated to the backing material layer 54 side among ultrasound signals emitted from a plurality of ultrasound transducers 48 or reflected propagated from the observation target. For this reason, the backing material is made of a material having rigidity, such as hard rubber, and an ultrasonic wave attenuation material (ferrite, ceramics, or the like) is added as needed.

The filler layer 80 is a layer with which the internal space 55 between the exterior member 41 and the backing material layer 54 is filled, and has a role of fixing the substrate 60, the non-coaxial cables 110, and various wiring portions. It is preferable that the acoustic impedance of the filler layer 80 matches the acoustic impedance of the backing material layer 54 with given accuracy or higher such that the ultrasound signals propagated from the ultrasound transducer array 50 to the backing material layer 54 side are not reflected at a boundary surface between the filler layer 80 and the backing material layer 54. It is preferable that the filler layer 80 is made of a member having heat dissipation to increase efficiency in dissipating heat generated in a plurality of ultrasound transducers 48. In a case where the filler layer 80 has heat dissipation, heat is received from the backing material layer 54, the substrate 60, the non-coaxial cables 110, and the like, and thus, heat dissipation efficiency can be improved.

With the ultrasound transducer unit 46 configured as described above, in a case where each ultrasound transducer 48 of the ultrasound transducer array 50 is driven, and a voltage is applied to the electrode 52 of the ultrasound transducer 48, the piezoelectric body 49 vibrates to sequentially generate ultrasonic waves, and the irradiation of the ultrasonic waves is performed toward the observation target part of the subject. Then, as a plurality of ultrasound transducers 48 are sequentially driven by an electronic switch, such as a multiplexer, scanning with ultrasonic waves is performed in a scanning range along a curved surface on which the ultrasound transducer array 50 is disposed, for example, a range of about several tens mm from the center of curvature of the curved surface.

In a case where the echo signal reflected from the observation target part is received, the piezoelectric body 49 vibrates to generate a voltage and outputs the voltage as an electric signal corresponding to the received ultrasound echo to the ultrasound processor device 14. Then, the electric signal is subjected to various kinds of signal processing in the ultrasound processor device 14 and is displayed as an ultrasound image on the monitor 20.

In the embodiment, the substrate 60 shown in FIG. 4 has, at one end, a plurality of electrode pads 62 that are electrically connected to a plurality of individual electrodes 52*a*, and a ground electrode pad 64 that is electrically connected to the transducer ground 52*b*. In FIG. 4, the cable 100 is omitted.

Electrical bonding of the substrate 60 and the individual electrodes 52*a* can be established by, for example, a resin material having conductivity. Examples of the resin material include an anisotropic conductive film (ACF) or an anisotropic conductive paste (ACP) obtained by mixing thermosetting resin with fine conductive particles and forming the mixture into a film.

As another resin material, for example, a resin material in which a conductive filler, such as metallic particles, is dispersed into binder resin, such as epoxy or urethane, and the filler forms a conductive path after adhesion may be used. Examples of this resin material include a conductive paste, such as a silver paste.

As shown in FIG. 3, the cable 100 comprises a plurality of non-coaxial cables 110, and an outer coat 102 with which a plurality of non-coaxial cables 110 are coated. Signal wires included in the non-coaxial cable 110 are electrically bonded to the electrode pads 62 of the substrate 60.

Next, a connection structure of the substrate 60 and the cable 100 will be described referring to the drawings.

Figure 5:
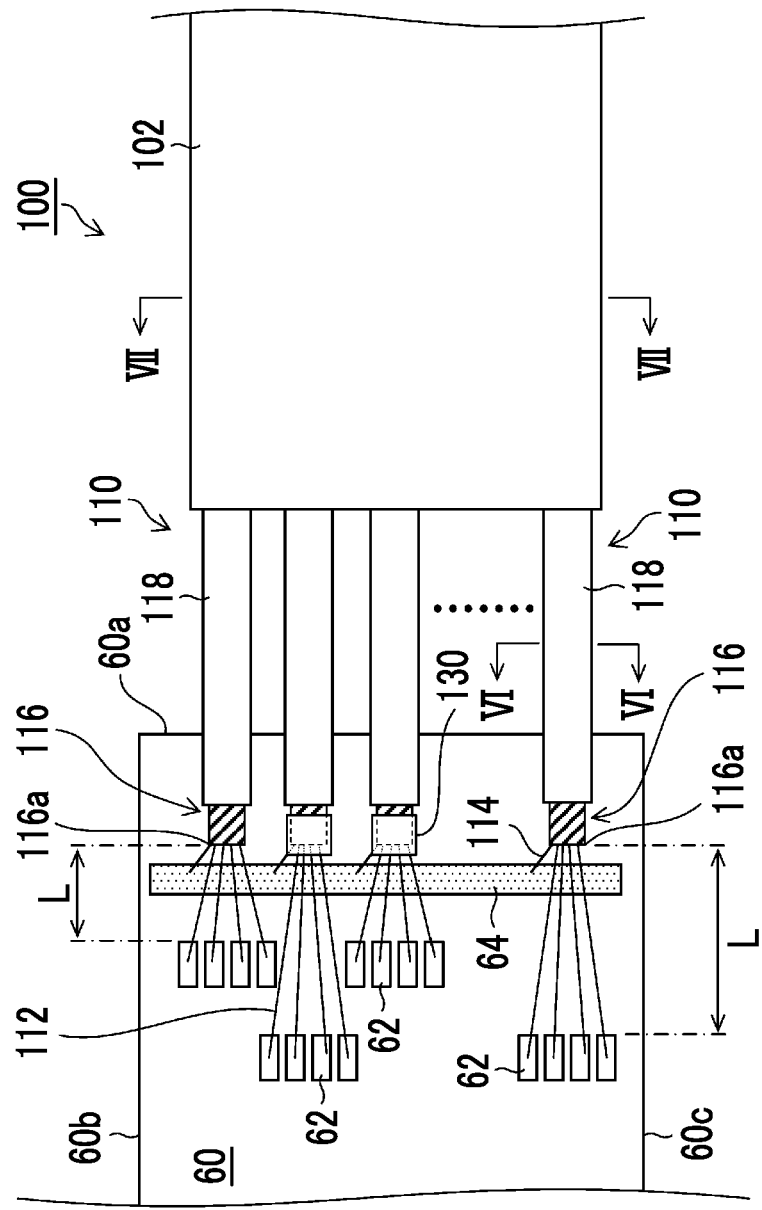
FIG. 5 is a diagram showing a connection structure of a substrate and non-coaxial cables.
Figure 6:
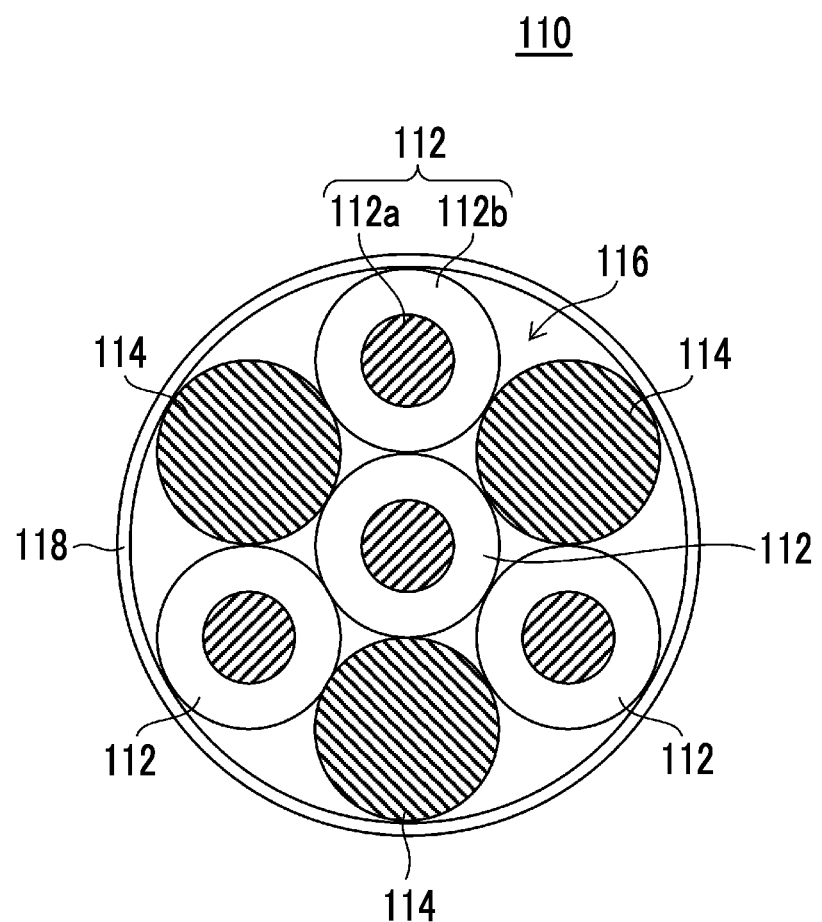
FIG. 6 is a cross-sectional view of a non-coaxial cable taken along the line VI-VI of FIG. 5.
Figure 7:
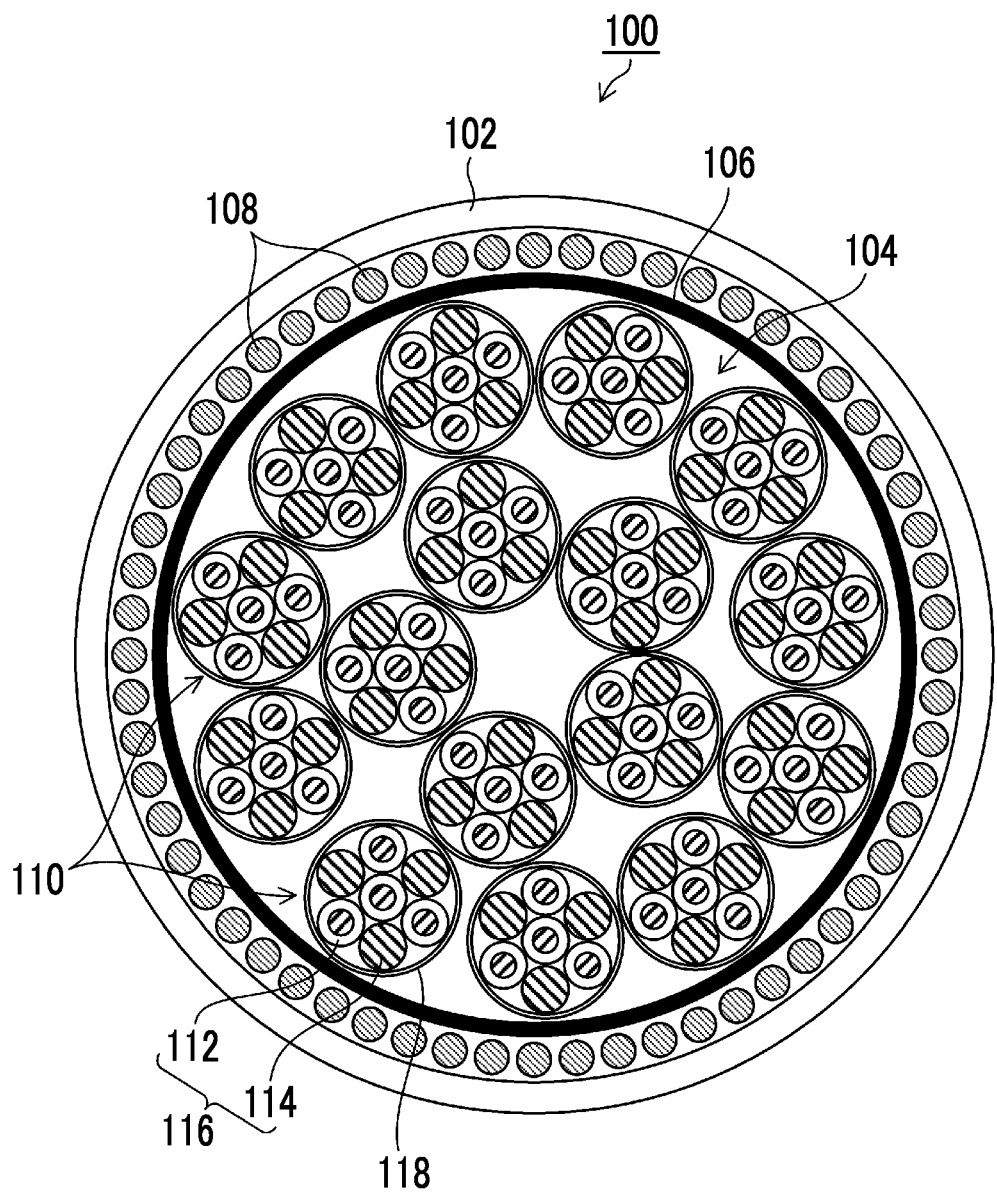
FIG. 7 is a cross-sectional view of a cable taken along the line VII-VII of FIG. 5.

FIG. 5 is an enlarged view of a portion including the substrate 60 and the cable 100. FIG. 6 is a cross-sectional view taken along the line VI-VI. FIG. 7 is a cross-sectional view taken along the line VII-VII.

As shown in FIG. 5, the substrate 60 has a plurality of electrode pads 62 disposed along a side 60*a* on a proximal end side, and the ground electrode pad 64 disposed between a plurality of electrode pads 62 and the side 60*a*. The ground electrode pad 64 is disposed in parallel to the side 60*a*.

The cable 100 is disposed at a position facing the side 60*a* of the substrate 60. The cable 100 comprises a plurality of non-coaxial cables 110, and the outer coat 102 that covers a plurality of non-coaxial cables 110. The electrode pads 62 and signal wires 112 of the non-coaxial cables 110 are electrically bonded. The non-coaxial cables 110 are disposed in parallel with a side 60*b* and a side 60*c* perpendicular to the side 60*a*. Note that a positional relationship between the substrate 60 and the non-coaxial cables 110 is not particularly limited.

Next, the structure of the non-coaxial cables 110 will be described. As shown in FIG. 6, each non-coaxial cable 110 has a plurality of signal wires 112 and a plurality of ground wires 114. Each signal wire 112 is made of, for example, a conductor 112*a*, and an insulating layer 112*b* with which the periphery of the conductor 112*a* is coated. The conductor 112*a* is made of, for example, an element wire, such as copper or copper alloy. The element wire is subjected to, for example, plating processing, such as tin plating or silver plating. The conductor 112*a* has a diameter of 0.03 mm to 0.04 mm.

The insulating layer 112*b* can be made of, for example, a resin material, such as fluorinated-ethylene-propylene (FEP) or perfluoroalkoxy (PFA). The insulating layer 112*b* has a thickness of 0.015 mm to 0.025 mm.

Each ground wire 114 is made of a conductor having the same diameter as the signal wire 112. The ground wire 114 is made of an element wire, such as copper or copper alloy, or a stranded wire obtained by stranding a plurality of element wires, such as copper or copper alloy.

A first cable bundle 116 is configured by stranding a plurality of signal wires 112 and a plurality of ground wires 114.

Each non-coaxial cable 110 comprises a first shield layer 118 with which the periphery of the first cable bundle 116 is coated. The first shield layer 118 can be made of an insulating film obtained by laminating metallic foils through an adhesive. The insulating film is made of a polyethylene terephthalate (PET) film. The metallic foil is made of an aluminum foil or a copper foil.

The non-coaxial cable 110 is shielded by the first shield layer 118 with a plurality of signal wires 112 as one set. The signal wires 112 are handled in a unit of the non-coaxial cable 110.

As shown in FIG. 6, in the non-coaxial cable 110 of the embodiment, the first cable bundle 116 is configured by stranding seven wires in total of four signal wires 112 and three ground wires. One signal wire 112 of the four signal wires 112 is disposed at the center. The remaining three signal wires 112 and the three ground wires 114 are disposed adjacently in the periphery of the signal wire 112 at the center. Note that the number of signal wires 112, the number of ground wires 114, and the disposition of the wires in the first cable bundle 116 are not limited to the structure of FIG. 6.

Next, the structure of the cable 100 will be described. As shown in FIG. 7, the cable 100 comprises a plurality of non-coaxial cables 110. A second cable bundle 104 is configured with a plurality of non-coaxial cables 110.

The second cable bundle 104 is coated with the outer coat 102. The outer coat 102 can be made of a fluorine-based resin material, such as extruded and coated PFA, FEP, an ethylene/ethylene tetrafluoride copolymer (ETFE), or polyvinyl chloride (PVC). The outer coat 102 can be made of a wound resin tape (PET tape). The coating of the second cable bundle 104 with the outer coat 102 includes a case where the outside of the second cable bundle 104 is coated directly and a case where the outside of the second cable bundle 104 is coated indirectly. Indirect coating includes disposing another layer between the outer coat 102 and the second cable bundle 104.

The cable 100 of the embodiment comprises, in order from the inside, a resin layer 106 and a second shield layer 108 between the outer coat 102 and the second cable bundle 104. The second cable bundle 104 is coated with the resin layer 106. The resin layer 106 can be made of, for example, the fluorine-based resin material or the resin tape described above.

The second shield layer 108 may be configured by, for example, braiding a plurality of element wires. The element wire is made of a copper wire, a copper alloy wire, or the like subjected to plating processing (tin plating or silver plating).

The cable 100 may not comprise both the resin layer 106 and the second shield layer 108 other than the above-described configuration or may comprise only one of the resin layer 106 or the second shield layer 108.

The cable 100 of the embodiment includes 16 non-coaxial cables 110, and includes 64 signal wires 112. The number of non-coaxial cables 110 and the number of signal wires 112 are not limited to the numerical values.

As described above, the non-coaxial cable 110 included in the cable 100 does not comprise a shield layer and an outer coat for each signal wire 112, unlike the coaxial cable in the related art. In particular, in a case where the cable 100 is configured with a plurality of non-coaxial cables 110, the cable 100 can be reduced in diameter compared to the coaxial cable in the related art. In a case where the outside diameter is the same as the outside diameter of the coaxial cable, the cable 100 can comprise a greater number of signal wires 112 than the coaxial cable in the related art.

Next, a connection structure of the substrate 60 and the non-coaxial cables 110 will be described in detail. As shown in FIG. 5, on the proximal end side of the substrate 60, the resin layer 106 (not shown), the second shield layer 108 (not shown), and the outer coat 102 of the cable 100 are removed, and a plurality of non-coaxial cables 110 are exposed. On the proximal end side of the substrate 60, the first shield layer 118 of each non-coaxial cable 110 is removed, and the first cable bundle 116 is exposed.

The first shield layer 118 is positioned on the substrate 60, and the substrate 60 and the first shield layer 118 overlap as viewed from a direction perpendicular to the substrate 60 (hereinafter, referred to as plan view). The first cable bundle 116 is exposed only on the substrate 60, and the substrate 60 and the first cable bundle 116 overlap only on the substrate 60. The first cable bundle 116 does not protrude from the substrate 60, and thus, a state in which a part of the first cable bundle is not superimposed on the substrate 60, that is, a state in which the whole first cable bundle 116 is superimposed on the substrate 60 is brought.

The substrate 60 and the first cable bundle 116 are fixed by a fixing part 130, and the relative positions of the substrate 60 and each first cable bundle 116 are fixed. The fixing part 130 fixes the substrate 60 and the first cable bundle 116 in a state overlapping only the substrate 60. The first cable bundle 116 configured with a stranded wire of a plurality of signal wires 112 and a plurality of ground wires 114 is unstranded into the respective signal wires 112 at a distal end 116a. Each unstranded signal wire 112 is electrically bonded to the electrode pad 62 disposed on the substrate 60. The distal end 116a is a start position where each signal wire 112 is unstranded. In some first cable bundles 116, the fixing part 130 is omitted for ease of understanding.

As described above, each signal wire 112 of the non-coaxial cable 110 is configured with the conductor 112a and the insulating layer 112b, and a shield layer is not provided for each signal wire 112, unlike a coaxial cable. For this reason, the signal wires 112 are likely to be disconnected at the time of a wiring work of electrically bonding the electrode pads 62 and the signal wires 112, subsequent handling, and an assembling step to the probe.

In the embodiment, the substrate 60 and the first cable bundle 116 are fixed by the fixing part 130. Accordingly, when stress is applied to the cable 100 or the non-coaxial cable 110, stress is prevented from being transmitted to a bonded portion of the electrode pad 62 and the signal wire 112, and disconnection of the signal wire 112 can be prevented.

The fixing part 130 is not particularly limited as long as the relative positions between the substrate 60 and the first cable bundle 116 can be fixed, and for example, any one of an adhesive, solder, or a clamp member, or a combination thereof can be applied. The fixing part 130 can individually fix the substrate 60 and the first cable bundle 116 or can fix the substrate 60 and a plurality of first cable bundles 116 in a lump.

The ground wires 114 of each first cable bundle 116 are electrically bonded to the ground electrode pad 64 of the substrate 60. At least one ground wire 114 included in each first cable bundle 116 is electrically bonded to the ground electrode pad 64. A plurality of ground wires 114 are in contact with each other in the first cable bundle 116. Accordingly, at least one ground wire 114 of each first cable bundle 116 is electrically bonded to the ground electrode pad 64, where the ground potentials of a plurality of first cable bundles 116 can be at the same potential. A region occupied by the wires can be reduced by reducing the number of ground wires 114 that are electrically bonded to the ground electrode pad 64. As a result, it is possible to achieve reduction in diameter of the distal end part 40.

In the connection structure shown in FIG. 5, the electrode pads 62 corresponding to each non-coaxial cable 110 are collectively disposed. That is, four electrode pads 62 that are electrically bonded to the four signal wires 112 are collectively disposed on the substrate 60. It is preferable that the electrode pads 62 corresponding to the non-coaxial cable 110 are the electrode pads 62 that are disposed in an extension direction of the non-coaxial cable 110. It is preferable that the signal wires 112 of each non-coaxial cable 110 are not electrically bonded to the electrode pads 62 of an adjacent non-coaxial cable 110. It is possible to prevent stress from being applied to the signal wires 112.

In the connection structure shown in FIG. 5, the positions of the electrode pads 62 connected to the signal wires 112 of the non-coaxial cable 110 are different between adjacent non-coaxial cables 110. In comparison of the electrode pads 62 corresponding to the non-coaxial cable 110 closest to the side 60b with the electrode pads 62 corresponding to the non-coaxial cable 110 second closest to the side 60b, a distance L from the distal end 116a of the first cable bundle 116 fixed by the fixing part 130 is different. There are two kinds of distances L different between the first cable bundles 116.

As a result, a plurality of electrode pads 62 corresponding to the signal wires 112 of the non-coaxial cable 110 are disposed in zigzags for every plurality of electrode pads 62 in plan view. It is possible to narrow an interval between a plurality of adjacent electrode pads 62, and to dispose a plurality of electrode pads 62 with high density compared to a case where a plurality of electrode pads 62 are not disposed in zigzags (a case where a plurality of electrode pads 62 are disposed linearly along the side 60a).

In the embodiment, although the two kinds of distances L are shown, two kinds or more of distances L can be set. It is possible to dispose a plurality of electrode pads 62 with higher density.

The length of the signal wire 112 is different between the first cable bundles 116 corresponding to the electrode pads 62 disposed in zigzags.

On the other hand, in a unit of the non-coaxial cables 110, the distance L between the electrode pads 62 corresponding to a plurality of signal wires 112 and the distal end 116a of the first cable bundle 116 are equal.

Figure 8:
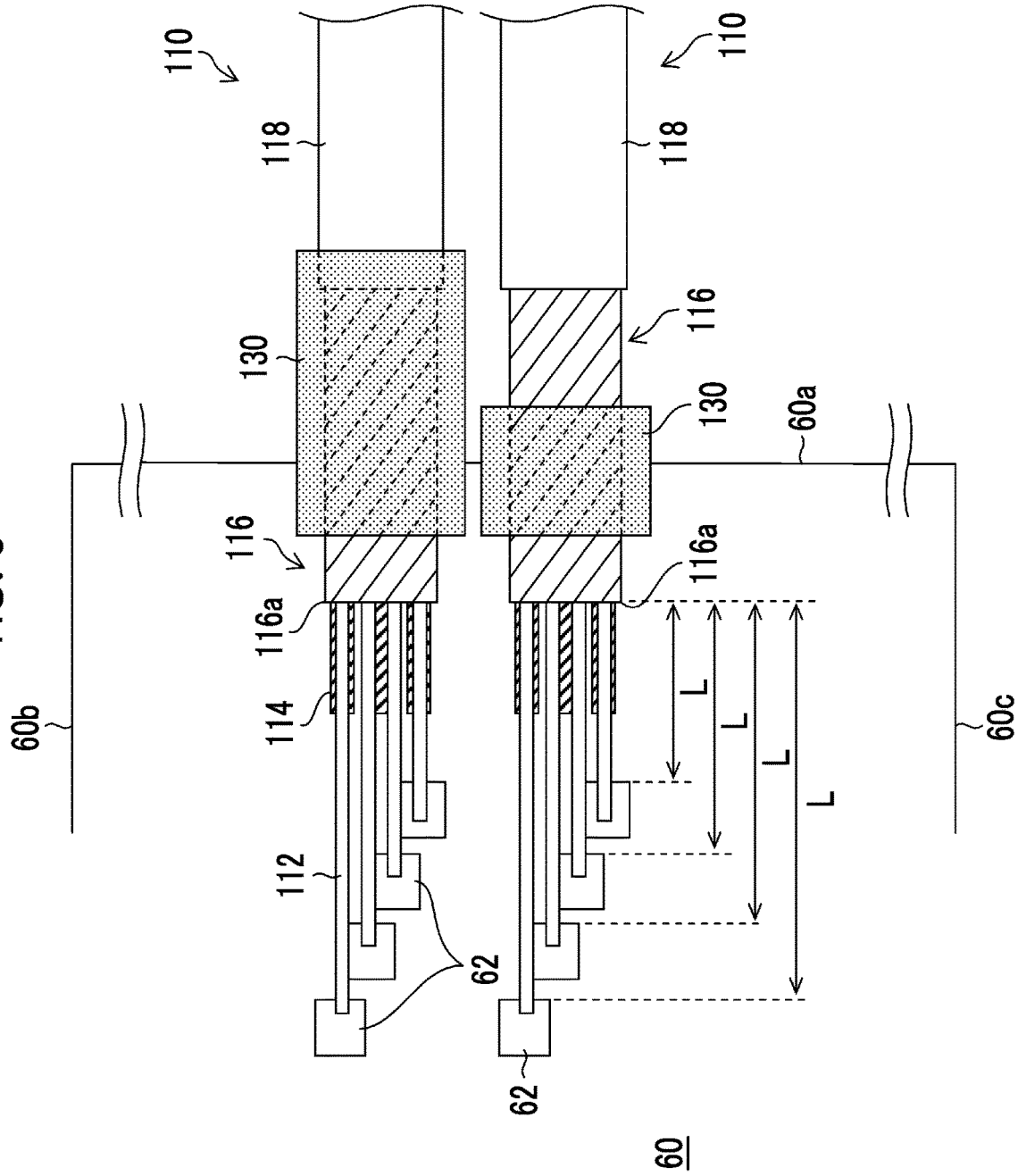
FIG. 8 is a diagram showing a first modification example of a connection structure of the substrate and the non-coaxial cable.

Next, another preferred connection structure will be described. FIG. 8 is a diagram showing a first modification example of a connection structure of the substrate and the non-coaxial cable. The same configurations as those in FIG. 5 are represented by the same reference numerals, and description thereof may not be repeated. As shown in FIG. 8, each non-coaxial cable 110 includes the first cable bundle 116 consisting of a plurality of signal wires 112 and a plurality of ground wires 114. There are four kinds of distances L between the electrode pads 62 of the substrate 60 corresponding to a plurality of signal wires 112 included in each first cable bundle 116 and the distal end 116a of the first cable bundle 116 fixed by the fixing part 130, for each first cable bundle 116. The ground electrode pad 64 is omitted.

As a result, in plan view, a plurality of electrode pads 62 corresponding to the first cable bundle 116 are sequentially disposed shifted along the longitudinal axis direction (a direction along the side 60b) of the cable, an arrangement pitch of the electrode pads 62 in a direction (a direction along the side 60a) perpendicular to the longitudinal axis direction of the cable is made small compared to FIG. 5, and a space occupied by the electrode pad 62 in the same direction is narrowed. It is possible to dispose a plurality of electrode pads 62 with high density for each first cable bundle 116. In FIG. 8, although the four kinds of distances L are shown, there may be two kinds or more of distances L, and the distance L may be different between adjacent electrode pads 62.

In FIG. 8, unlike the connection structure of FIG. 5, the first shield layer 118 does not overlap the substrate 60 in plan view. A position where the first cable bundle 116 is exposed from the first shield layer 118 is not particularly limited as long as the relative positions of the substrate 60 and the first cable bundle 116 can be fixed by the fixing part 130.

The first shield layer 118 does not overlap the substrate 60 in plan view. On the other hand, the first cable bundle 116 is not exposed only on the substrate 60, and is exposed in a state protruding from the substrate 60. That is, the first cable bundle 116 is fixed by the fixing part 130 in a state of being partially superimposed on the substrate 60.

The fixing part 130 fixes the relative positions of the substrate 60 and the first cable bundle 116 in a state of being partially superimposed on the substrate 60. The position and the size of the fixing part 130 are not limited as long as the relative positions of the substrate 60 and the first cable bundle 116 can be fixed. The fixing part 130 may perform fixing while including the first shield layer 118 or may not include the first shield layer 118.

In FIG. 8, in a case of electrically bonding the signal wires 112 to the electrode pads 62 at different distances L, it is preferable that, for the signal wire 112 smaller in electric capacity per unit length among the signal wires 112 of the first cable bundle 116, the distance L between the electrode pad 62 and the distal end 116a of the first cable bundle 116 is longer.

The electric capacity of the signal wire 112 has an influence on the sensitivity of the ultrasound transducer 48 to which the signal wire 112 is electrically connected. The sensitivity has an influence on image quality deterioration of an ultrasound image. Therefore, it is preferable that a difference in electric capacity between the signal wires 112 of the first cable bundle 116 is small.

In a case where the signal wires 112 of the first cable bundle 116 are at least unequal in electric capacity per unit length, the signal wire 112 that is smaller in electric capacity per unit length is longer in length. As the signal wire 112 is longer, the electric capacity is greater. On the other hand, even though the signal wire 112 that is small in electric capacity per unit length is made long to increase the whole electric capacity, a difference in whole electric capacity from another signal wire 112 that is large in electric capacity per unit length can be reduced. In a case where the electric capacity per unit length is different between the signal wires 112 of the first cable bundle 116, with the application of the lengths of the signal wires 112 described above, it is possible to suppress variation of sensitivity.

Figure 9A:
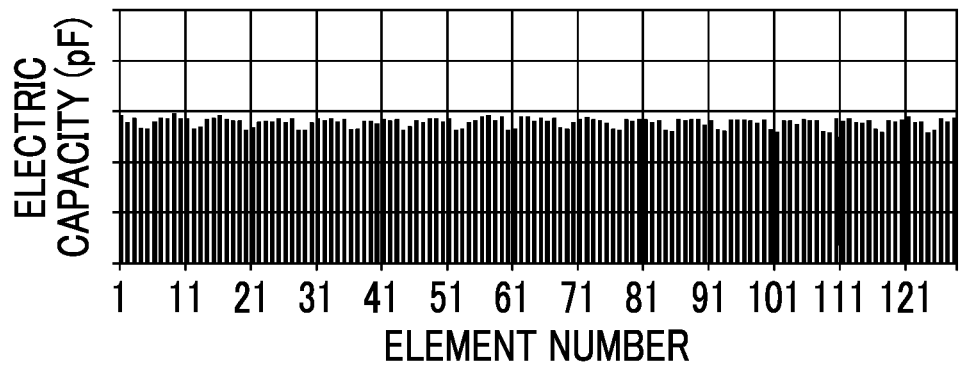
FIGS. 9A and 9B are graphs showing a relationship between an ultrasound transducer and electric capacity.
Figure 9B:
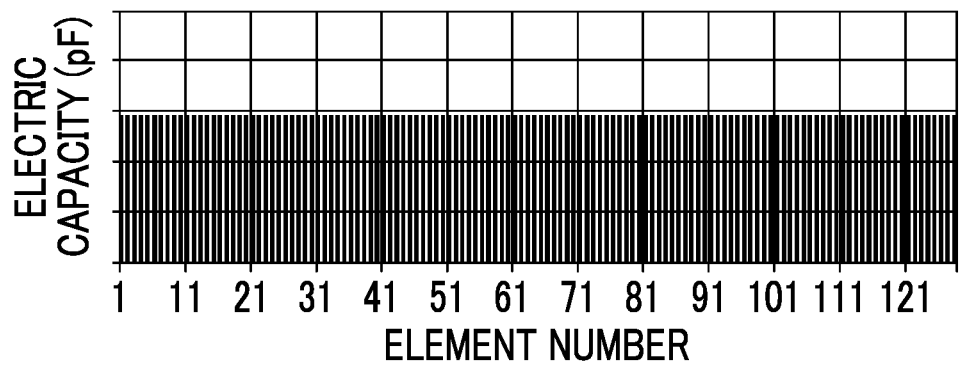

Next, a relationship between an ultrasound transducer and electric capacity will be described based on graphs. FIGS. 9A and 9B are graphs showing a relationship between an ultrasound transducer and electric capacity. The vertical axis indicates electric capacity (pF), and the horizontal axis indicates an element number of an ultrasound transducer. The element number indicates a number allocated to identify each ultrasound transducer 48. The graphs indicate the electric capacity of the signal wire 112 connected to each ultrasound transducer 48. In FIG. 9A, the electric capacity per unit length of each signal wire 112 is different for each first cable bundle 116. For this reason, even though the signal wires 112 included in the first cable bundle 116 are constant in length, as shown in the graph, the whole electric capacity of each signal wire 112 is not constant. There is a difference in whole electric capacity between the signal wires 112, and variation occurs.

In FIG. 9B, the lengths of the signal wires 112 included in the first cable bundle 116 are not constant, and the length of the signal wire 112 that is small in electric capacity per unit length is extended. As a result, the electric capacity of the extended signal wire 112 increases. On the other hand, a difference in whole electric capacity between the signal wires 112 is reduced, and variation is suppressed.

In a case of the non-coaxial cable 110, the signal wire 112 may be influenced by the magnitude of the electric capacity depending on the disposition in the first cable bundle 116. For example, as shown in FIG. 6, the electric capacity per unit length of the signal wire 112 disposed at the center of the non-coaxial cable 110 is made smaller than the electric capacity per unit length of a plurality of signal wires 112 disposed in the periphery. This means that, in a case where the signal wires 112 are equal in length, the electric capacity of the signal wire 112 disposed at the center is made small. Accordingly, as the signal wire 112 disposed at the center is made long, it is possible to reduce the difference in electric capacity from the signal wires 112 disposed in the periphery.

Figure 10:
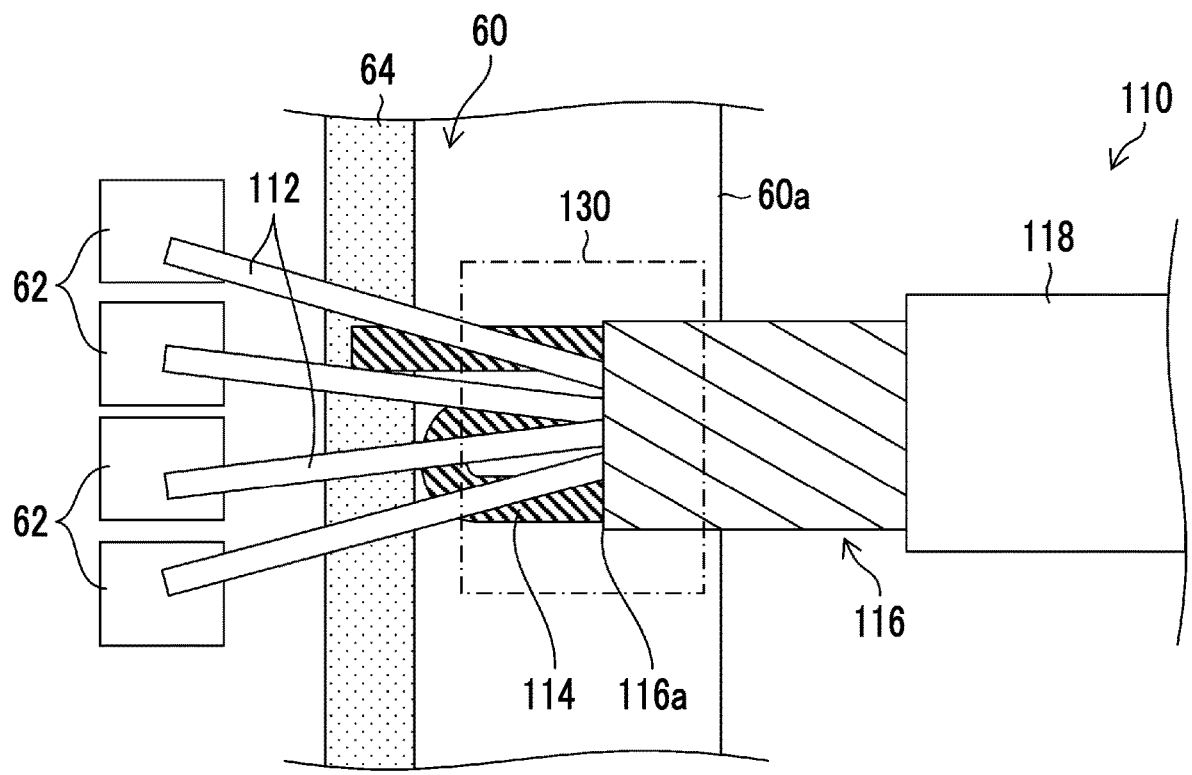
FIG. 10 is a diagram showing a second modification example of a connection structure of the substrate and the non-coaxial cable.

Next, another preferred connection structure will be described. FIG. 10 is a diagram showing a second modification example of a connection structure of the substrate and the non-coaxial cable. The same configurations as those in FIGS. 5 and 8 are represented by the same reference numerals, and description thereof may not be repeated.

As shown in FIG. 10, the non-coaxial cable 110 includes the first cable bundle 116 consisting of a plurality of signal wires 112 and a plurality of ground wires 114. A plurality of signal wires 112 included in each first cable bundle 116 and the electrode pads 62 corresponding to the signal wires 112 are electrically bonded. The ground electrode pad 64 and the ground wires 114 are electrically bonded. On the other hand, the ground wires 114 that are not electrically bonded to the ground electrode pad 64 are connected.

In FIG. 10, a part of the first cable bundle 116 is superimposed on the substrate 60. On the other hand, in a state in which the fixing part 130 is superimposed only on the substrate 60, the relative positions of the substrate 60 and the first cable bundle 116 are fixed. As long as the relative positions of the substrate 60 and the first cable bundle 116 can be fixed, a positional relationship of the substrate 60, the first cable bundle 116, and the fixing part 130 is not limited.

Figure 11:
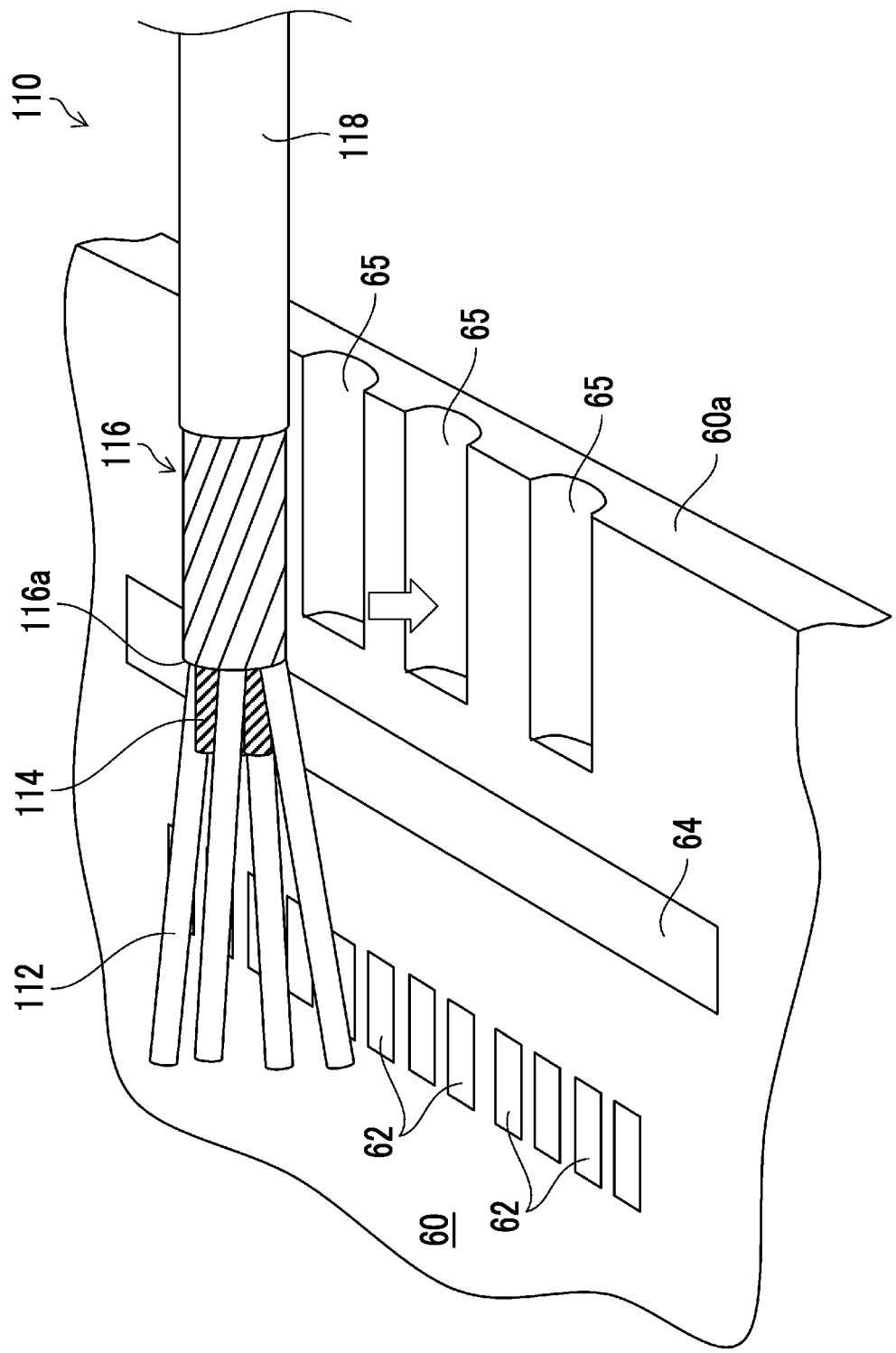
FIG. 11 is a diagram showing a third modification example of a connection structure of the substrate and the non-coaxial cable.

Next, another preferred connection structure will be described. FIG. 11 is a diagram showing a third modification example of a connection structure of the substrate and the non-coaxial cable. The same configurations as those in FIGS. 5, 8, and 10 are represented by the same reference numerals, and description thereof may not be repeated. As shown in FIG. 11, the non-coaxial cable 110 includes the first cable bundle 116 consisting of a plurality of signal wires 112 and a plurality of ground wires 114. The electrode pads 62 corresponding to the signal wires 112 are disposed on the substrate 60. Grooves 65 are provided in the substrate 60. Since the first cable bundle 116 is accommodated in the groove 65, the first cable bundle 116 is stably held by the groove 65. It is preferable that the groove 65 follows the shape of the outer periphery of the first cable bundle 116. The groove 65 may follow a part of the outer periphery of the first cable bundle 116. The groove 65 is decided from the positions of the first cable bundle 116 and the electrode pad 62 corresponding to the first cable bundle 116. The first cable bundle 116 is held toward the corresponding electrode pad 62 by the groove 65.

Figure 12:
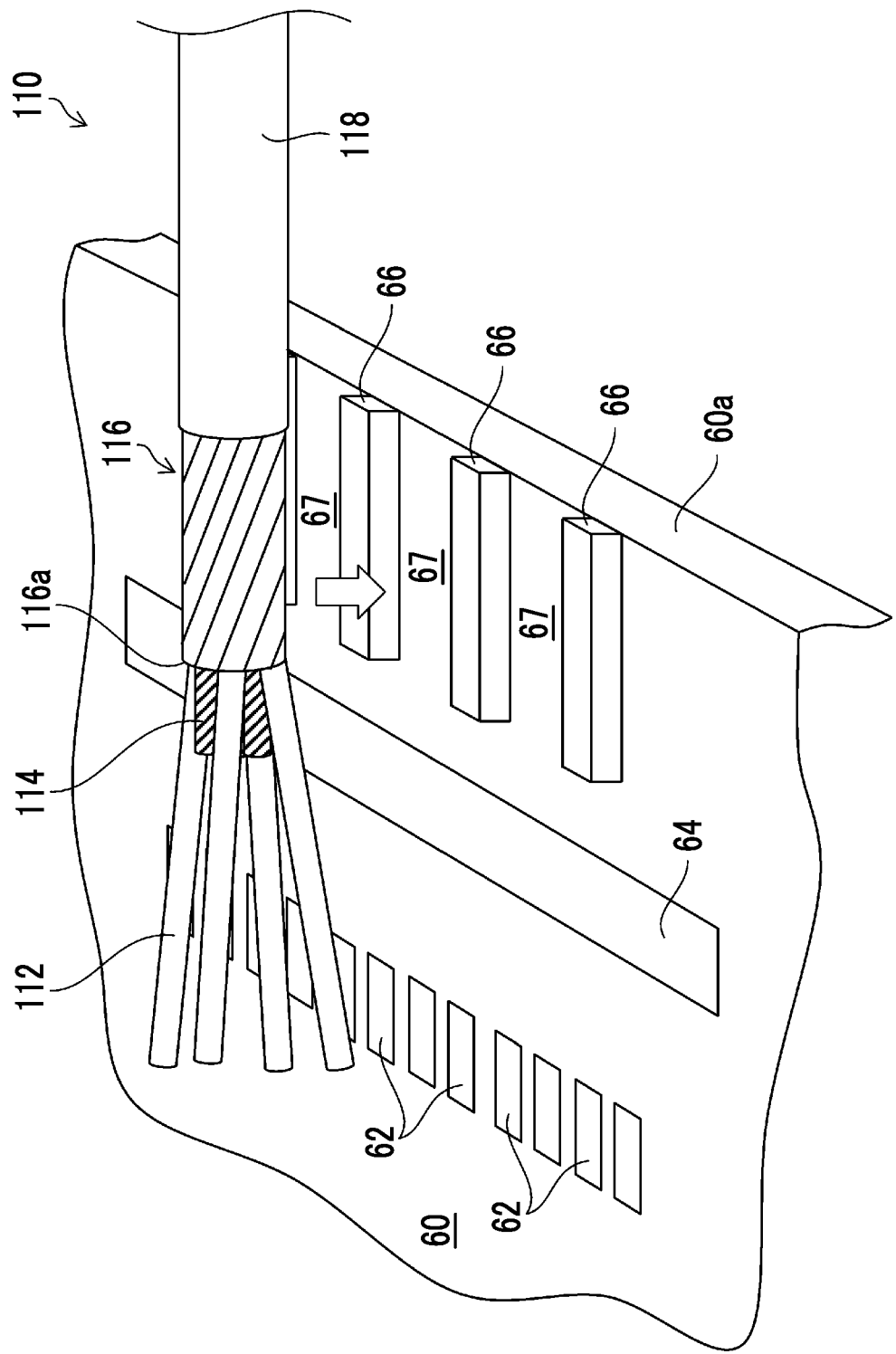
FIG. 12 is a diagram showing a fourth modification example of a connection structure of the substrate and the non-coaxial cable.

In FIG. 11, although the grooves 65 are provided in the substrate 60, the substrate 60 can be given the function of the grooves 65 by separate members from the substrate 60. FIG. 12 is a diagram showing a fourth modification example of a connection structure of the substrate and the non-coaxial cable. For example, as shown in FIG. 12, a plurality of wall members 66 that are perpendicular to the side 60a and extend from the side 60a toward the electrode pads 62 can be provided on a surface of the substrate 60 on which the electrode pads 62 are disposed. Grooves 67 are formed on the substrate 60 by adjacent wall members 66. Since the first cable bundle 116 is accommodated in the groove 67, the first cable bundle 116 is stably held by the groove 67.

Although the invention has been described, the invention is not limited to the above-described example, and various improvements or modifications may be of course made without departing from the spirit and scope of the invention.

EXPLANATION OF REFERENCES

10: ultrasonography system
12: ultrasound endoscope
14: ultrasound processor device
16: endoscope processor device
18: light source device
20: monitor
21a: water supply tank
21b: suction pump
22: insertion part
24: operating part
26: universal cord
28a: air and water supply button
28b: suction button
29: angle knob
30: treatment tool insertion port
32a: connector
32b: connector
32c: connector
34a: air and water supply tube
34b: suction tube
36: ultrasound observation part
38: endoscope observation part
40: distal end part
41: exterior member
42: bending part
43: flexible part
44: treatment tool lead-out port
45: treatment tool channel
46: ultrasound transducer unit
47: laminate
48: ultrasound transducer
49: piezoelectric body
50: ultrasound transducer array
52: electrode
52a: individual electrode
52b: transducer ground
54: backing material layer
55: internal space
60: substrate
60a: side
60b: side
60c: side
62: electrode pad
64: ground electrode pad
65: groove
66: wall member
67: groove
76: acoustic matching layer
78: acoustic lens
80: filler layer
82: observation window
84: objective lens
86: solid-state imaging element
88: illumination window
90: cleaning nozzle
92: wiring cable
100: cable
102: outer coat
104: second cable bundle
106: resin layer
108: second shield layer
110: non-coaxial cable
112: signal wire
112a: conductor
112b: insulating layer
114: ground wire
116: first cable bundle
116a: distal end
118: first shield layer
130: fixing part

What is claimed is:

1. An ultrasound endoscope comprising:
   an insertion part that includes a distal end part having an ultrasound transducer array in which a plurality of ultrasound transducers are arranged;
   a cable that is inserted into the insertion part; and
   a substrate that electrically connects the plurality of ultrasound transducers and the cable, and is disposed in the distal end part,
   wherein the cable has
   a non-coaxial cable that includes a first cable bundle consisting of a plurality of signal wires and a plurality of ground wires, and a first shield layer with which the first cable bundle is coated, and
   an outer coat with which a second cable bundle consisting of a plurality of the non-coaxial cables is coated,
   the substrate includes a plurality of electrode pads connected to the plurality of ultrasound transducers, respectively,
   each first cable bundle is individually led out from the cable, and each signal wire of the first cable bundle is led out and electrically bonded to the corresponding electrode pad of the substrate, and
   a fixing part that fixes relative positions of the substrate and each first cable bundle is provided.

2. The ultrasound endoscope according to claim 1, wherein the cable includes a second shield layer with which the second cable bundle is coated, between the outer coat and the second cable bundle.

3. The ultrasound endoscope according to claim 2, wherein the cable includes a resin layer with which the second cable bundle is coated, between the second cable bundle and the second shield layer.

4. The ultrasound endoscope according to claim 1, wherein the cable includes a resin layer with which the second cable bundle is coated, between the outer coat and the second cable bundle.

5. The ultrasound endoscope according to claim 3, wherein the resin layer is made of a fluorine-based resin material.

6. The ultrasound endoscope according to claim 1, wherein the fixing part is any one of an adhesive, solder, or a clamp member, or a combination thereof.

7. The ultrasound endoscope according to claim 1, wherein the fixing part fixes the substrate and each first cable bundle in a state in which a part of the first cable bundle is superimposed on the substrate.

8. The ultrasound endoscope according to claim 1, wherein the fixing part fixes the substrate and each first cable bundle in a state in which a part of the first cable bundle is not superimposed on the substrate.

9. The ultrasound endoscope according to claim 1, wherein the substrate is any one of a rigid substrate or a flexible substrate.

10. The ultrasound endoscope according to claim 1, wherein distances between the electrode pads of the substrate corresponding to the plurality of signal wires included in each first cable bundle and a distal end of the first cable bundle fixed by the fixing part are equal for each first cable bundle.

11. The ultrasound endoscope according to claim 1, wherein there are two kinds or more of distances between the electrode pads of the substrate corresponding to the plurality of signal wires included in each first cable bundle and a distal end of the first cable bundle fixed by the fixing part, for each first cable bundle.

12. The ultrasound endoscope according to claim 1, wherein the substrate has a ground electrode pad, and at least one ground wire included in each first cable bundle is electrically bonded to the ground electrode pad.

13. The ultrasound endoscope according to claim 12, wherein the ground wires that are included in each first cable bundle and are not bonded to the ground electrode pad are connected between the ground electrode pad and the distal end of the first cable bundle fixed by the fixing part.

14. The ultrasound endoscope according to claim 10, wherein there are two kinds or more of the distances different between the first cable bundles.

15. The ultrasound endoscope according to claim 11, wherein the signal wires included in the first cable bundle are at least unequal in electric capacity per unit length, and
   for the signal wire smaller in the electric capacity per unit length among the signal wires of the first cable bundle, the distance between the electrode pad and the distal end of the first cable bundle fixed by the fixing part is longer.

16. The ultrasound endoscope according to claim 1, wherein the substrate has grooves that hold the first cable bundles.

* * * * *